United States Patent [19]

Sankey

[11] Patent Number: 5,932,720

[45] Date of Patent: Aug. 3, 1999

[54] SOLID SUCRALOSE

[75] Inventor: George Henry Sankey, Earley, United Kingdom

[73] Assignee: Tate & Lyle Public Limited Company, United Kingdom

[21] Appl. No.: 09/011,845

[22] PCT Filed: Jul. 18, 1996

[86] PCT No.: PCT/GB96/01729

§ 371 Date: Feb. 18, 1998

§ 102(e) Date: Feb. 18, 1998

[87] PCT Pub. No.: WO97/08181

PCT Pub. Date: Mar. 6, 1997

[30] Foreign Application Priority Data

Aug. 23, 1995 [GB] United Kingdom .................. 9517281

[51] Int. Cl.⁶ ........................................................ C07H 1/00
[52] U.S. Cl. .................... 536/124; 536/122; 536/123.13; 536/127

[58] Field of Search .............................. 536/4.1, 119, 124, 536/127, 123.13, 122

[56] References Cited

U.S. PATENT DOCUMENTS 5,498,709 3/1996 Navia et al. ............................. 536/124

FOREIGN PATENT DOCUMENTS 1543167 3/1979 United Kingdom .
2065646 7/1981 United Kingdom .

*Primary Examiner*—Elli Peselev
*Attorney, Agent, or Firm*—Ostrolenk, Faber, Gerb & Soffen, LLP

[57] ABSTRACT

The flowability of crystalline sucralose can be increased by treating the crystalline material in a fluidised bed at ambient temperature with additions of water, followed by a fluidised drying phase. Fluidisation by means of an upward current of air at 25–35° C. and added water at 20–50% by weight, e.g., 25–40%, is preferred.

16 Claims, No Drawings

SOLID SUCRALOSE

This invention relates to the preparation of solid crystalline sucralose having improved flow characteristics and appearance. Sucralose (4-chloro-4-deoxy-α-D-galactopyranosyl 1.6-dichloro-1.6-dideoxy-β-D-fructofuranoside, otherwise known as 4,1', 6'-trichloro4, 1',6'-trideoxyealacto sucrose) is a potent sweetener originally disclosed in GB 1543167. Crystalline sucralose was disclosed in GB 2065646A in the form of orthorhombic needles. It is a problem of crystalline materials of this type. that because the needle-like structure tends to bind together to form mats, thev are thus difficult to transfer from one container to another. It is difficult to produce free-flowing sucralose, even under closely controlled laboratory conditions, and on large scale plant the problem is aggravated by the fact that the subsequent processing equipment such as pumps, centrifuges and drvers tends to fracture the crvstals, thus further harming the flow properties. There is thus a need for pure sucralose having a modified structure with improved flow properties.

The flow behaviour of solids is conventionally assessed in terms of flow speeds and also in terms of the angle of repose of the poured material. In Bulk Solids Handling: An Introduction To Practice And Technology, by C R Woodcock and J S Mason, Leonard Hill, Julv 1987, page 31, the flow behaviour of particulate solids is crudely classified in terms of the angle of repose as follows:

25 –30° very free-flowing

30 –38° free-flowing

38 –45° fair

45–55° cohesive

Greater than 55° very cohesive

From this it will be seen that a free-flowing material should have an angle of repose not exceeding about 38° and it is an object of the present invention to provide sucralose having an angle of repose tvpically below 40° and preferably within the range of 34 –38°. Flow behaviour for a particulate solid can also be more directly measured by a funnel test in which a sample of the material is timed as it flows through a funnel of known dimensions (as described below with reference to the Examples and in Bulk Solids Handling (ibid)).

We have now found that crystalline sucralose obtained directly from the final crystallisation stage of the synthetic process can be treated by a simple operation using standard equipment to provide considerably enhanced flow characteristics. The nature of the changes taking place in the material appear to be relatively complex and varied. It appears that the treatment removes fines and modifies the size and shape of individual crystals, providing a narrower particle size distribution and crystals of a chunkier, more cubic shape. The treated product may actually have a larger overall particle size, but this is not always the case. In particular, it should be noted that the process is not an agglomeration process in which small particles become stuck together, but more a process of crystal redefinition.

According to the present invention there is provided a method of treating crystalline sucralose to remove fines and to modify the size and shape of individual crystals so as to lower the angle of repose and to increase the flowability, comprising treating the crystalline material in a fluidised bed at ambient temperature with additions of water, followed by drying the crystalline material while it is fluidised. Typically, fluidisation is achieved by an upward current of an appropriate carrier gas, typically air. The process can be carried out in conventional fluidised bed drivers and granulators for example the MP2 (Niro Limited) which consists of four main areas:

an inlet air conditioning system:

modularised containers for the above applications;

a liquid dosing system; and an exhaust air system.

The drying air is drawn in by a fan through an inlet filter and heated by passing it over a steam heat exchanger. Temperature control is achieved by mixing hot air from the heat exchanger with ambient air via a valve.

The sucralose is placed in the product container and fluidised in a stream of warm air. The water is sprayed using a top spray two fluid nozzle onto the fluidised bed. The product is therefore modified and dried in one operation.

The water is fed to the nozzle using a peristaltic pump. The exhaust air is passed through a filter to prevent the product leaving the process chamber. The amount of water added, and the length of time of treatment may be varied within relatively wide ranges to provide products of particular specifications. In general, water should be added at a rate of from 20–50%, preferably 25–40%, most preferably 25–30% by weight of material during a treatment time of up to 4 hours, typically from 15 minutes to 2 hours. e.g. from 1 to 1.5 hours, at a bed temperature of, say, 25–35° C., e.g. about 30° C. before the final drying step.

Preferably, the starting material is screened to remove outsize pieces, and typical starting materials will have an average diameter of 100–200 mm. a co-efficient of variation (CV) of particle size of at least 38–48% (although material with a co-efficient of variation as low as 44% can still be improved) and an angle of repose of 38–48°.

As described in Crystallisation. 3rd Edition, J W Mullin, Butterworth and Heinemann, 1993. particle size distributions (PSDs) may be conveniently classified by the median size and the coefficient of variation. The CV. which quantifies the size spread is a statistical property related to the standard deviation of a Gaussian distribution and is normally expressed as a percentage by $$CV = 100\left(\frac{L_{84\%} - L_{16\%}}{2L_{50\%}}\right)$$

The values of $L_{84\%}$, $L_{50\%}$ ($=L_M$) and $L_{16\%}$ may be obtained from a cumulative mass distribution curve. The higher the CV the broader the spread, CV =0 denoting a single-sized distribution. The CV for a Gaussian distribution is 52%, but the product from a sugar crystallizer, which generally conforms more to a gamma function distribution. has a CV of about 50%.

The PSDs were measured by laser light scattering using the Malvern Mastersizer.

By way of example, a number of experiments were carried out using four different starting materials, SM1, SM2, SM3 and SM4, generally at a scale of approximately 12 kg. Examples 6 and 10 show the results of smaller scale experiments with higher amounts of water added.

The angle of repose was measured as the poured angle of repose (i.e. the angle between the horizontal base and a sloping side of a conical heap poured gently from a funnel onto a flat surface. The speed of flow was measured as follows.

Equipment

Powder funnel with a stem 25 mm in length and 22 mm in diameter.

Stop clock

Procedure

1. Place the funnel in a stand such that the top of the stem is 20 cm above the height of the bench.
2. Weigh 50 g of sample into a clean dry 500 ml beaker.
3. Insert a bung into the bottom of the funnel and then pour the weighed sample into the top of the funnel. Place the beaker under the stem.
4. Remove the bung and record the time taken for the sample to pass through the stem. Repeat this measurement twice more and record an average of the three timings.
5. If some sample remains adhering to the funnel, record the weight of sample which passes through the stem. This will give an indication of the amount of sample remaining in the funnel.
6. If the sample does not flow through the stem. tap the top of the funnel. If this causes the sample to pass through the funnel, the timings should be repeated with the top of the funnel being gently tapped. A note that tapping was necessary must be recorded alongside the timings. If the material does not pass through the funnel even with tapping, it should be reported as not flowing. Table 1 shoes the typical running conditions, illustrated for Examples 1, 2, 3 and 5, while Table 2 shows the results obtained for Examples 1 to 11.

It will be seen that the treatment considerably reduces the angle of repose and provides good flow characteristics. Furthermore, the product obtained is generally a shiny crystalline material of bright appearance, resembling caster (fine crystal) sugar.

TABLE 1

OPERATIONAL DATA AND TEST RESULTS

| Example No. | 1 | 2 | 3 | 5 |
|---|---|---|---|---|
| Starting Material | SM1 | SM1 | SM1 | SM2 |
| Temperature During Spraying | | | | |
| Inlet (° C.) | 62–63 | 62–64 | 62–66 | 64–66 |
| Bed (° C.) | 28–28 | 29–35 | 29–35 | 26–37 |
| Exhaust (° C.) | 25–27 | 26–27 | 26–28 | 24–31 |
| Duration of Spraying | 1 h 17 m | 1 h 18 m | 1 h 16 m | 1 h 8 m |
| Temperature During Drying | | | | |
| Inlet (° C.) | 63 | 62 | 62 | 61–66 |
| Bed (° C.) | 28–38 | 29–39 | 29–39 | 26–39 |

TABLE 1-continued

OPERATIONAL DATA AND TEST RESULTS

| Example No. | 1 | 2 | 3 | 5 |
|---|---|---|---|---|
| Exhaust (° C.) | 25 | 27 | 26–28 | 23 |
| Duration of Drying | 6 m | 4 m | 4 m | 5 m |
| Atomizing Pressure (bar g) | 2.0 | 2.0 | 2.0 | 2.0 |
| Amount of Water Added (g) | 3200 | 3200 | 3200 | 3200 |
| Spray Rate (g/min) | 39–45 | 40–43 | 40–43 | 43–50 |
| Charge Weight (kg) | 12.388 | 12.420 | 12.400 | 12.433 |
| Final Weight (kg) | 11.574 | 12.680 | 12.509 | 11.807 |
| Moisture (%)* | 0 | 0 | 0 | 0 |

*Determined by loss in weight on a Mettler Infra Red Moisture Meter at 55° C./10 mins

TABLE 2

| Batch | Scale (kg) | PSD (microns) | | | CV % | Bulk density g/ml | | Water added | Resdiual $H_2O$ (%) | Angle of repose (degrees) | Flow test (Sec) |
|---|---|---|---|---|---|---|---|---|---|---|---|
| | | $D(L_{16\%})$ | $D(L_{84\%})$ | $D(L_{50\%})$ | | Test 1 | Test 2 | | | | |
| SM1 | | 61.0 | 185.2 | 117.1 | 53.1 | 0.74 | 0.8 | | <0.1 | 42.8 | <2 |
| Ex 1 | 12.4 | 69.8 | 177.7 | 118.2 | 45.7 | 0.74 | 0.85 | 26 | <0.1 | — | <2 |
| Ex 2 | 12.4 | 60.9 | 173.5 | 109.7 | 51.4 | 0.75 | 0.85 | 26 | <0.1 | 36.2 | <2 |
| Ex 3 | 12.4 | 65.4 | 173.7 | 112.9 | 48.0 | 0.76 | 0.87 | 26 | <0.1 | — | <2 |
| Ex 4 | 12.4 | 71.7 | 188.3 | 123.0 | 47.4 | 0.75 | 0.85 | 26 | <0.1 | — | <2 |
| SM2 | | 114.0 | 283.0 | 191.0 | 44.2 | 0.82 | 0.89 | | — | 38.5 | <2 |
| Ex 5 | 12.4 | 157.0 | 337.0 | 240.0 | 37.5 | 0.75 | 0.82 | 26 | <0.1 | 35.2 | <2 |
| SM3 | | 76.1 | 220.5 | 147.6 | 48.9 | 0.72 | 0.78 | | <0.2 | 46.2 | no flow |
| Ex 6 | 0.96 | 61.0 | 202.3 | 129.5 | 54.5 | 0.8 | 0.9 | 40 | <0.5 | — | 1 |
| Ex 7 | 12.5 | 103.8 | 246.6 | 163.9 | 43.5 | 0.76 | 0.87 | 26 | 0.14 | 36.7 | <1 |
| Ex 8 | 12.5 | 100.5 | 239.9 | 162.5 | 50.8 | 0.74 | 0.87 | 26 | 0.17 | 38 2 | <1 |
| Ex 9 | 12.5 | 115.1 | 280.1 | 180.3 | 38.7 | 0.76 | 0.87 | 26 | 0.18 | 37.2 | <1 |
| SM4 | | 61.5 | 193.3 | 118.0 | 55.8 | 0.69 | 0.73 | | 0.1 | 45.5 | no flow |
| Ex 10 | 1.0 | 60.9 | 186.6 | 116.3 | 54.0 | — | — | 40 | — | 36.4 | — |
| Ex 11 | 11.5 | 72.8 | 200.7 | 124.8 | 51.2 | 0.77 | 0.84 | 26 | <0.1 | 36.4 | <2 |

I claim:

1. A method of treating crystalline sucralose to remove fines and to modify the size and shape of individual crystals so as to lower the angle of repose and to increase the flowability, comprising fluidizing the crystalline material in a fluidised bed at a temperature of 25–35° C. with additions of water, followed by drying the crystalline material while it is fluidised.

2. A method according to claim 1, in which fluidisation is achieved by an upward current of a carrier gas.

3. A method according to claim 1 or 2, in which water is added at a rate of from 20–50% by weight of material during a treatment time of up to 4 hours.

4. A method according to claim 3, in which water is added at a rate of from 25–40% by weight of material during a treatment time of 15 minutes to 2 hours.

5. A method according to claim 3, in which water is added at a rate of from 25–30% by weight of material during a treatment time of 1 to 1.5 hours.

6. A method according to claim 5, in which the starting material has an average diameter of 100–200 mm, a coefficient of variation (CV) of particle size of at least 48% and an angle of repose of 38–48.

7. A method according to claim 4, in which the starting material has an average diameter of 100–200 mm, a coefficient of variation of particle size of at least 48% and an angle of repose of 38–48°.

8. A method according to claim 3, in which the starting material has an average diameter of 100–200 mm, a coefficient of variation of particle size of at least 48% and an angle of repose of 38–48°.

9. A method according to claim 2, in which the starting material has an average diameter of 100–200 mm, a coefficient of variation of particle size of at least 48% and an angle of repose of 38–48°.

10. A method according to claim 1, in which the starting material has an average diameter of 100–200 mm, a coefficient of variation of particle size of at least 48% and an angle of repose of 38–48°.

11. A method according to claim 2, in which water is added at a rate of from 20–50% by weight of material during a treatment time of up to 4 hours.

12. A method according to claim 11, in which the starting material has an average diameter of 100–200 mm, a coefficient of variation (CV) of particle size of at least 48% and an angle of repose of 38–48°.

13. A method according to claim 11, in which water is added at a rate of from 25–40% by weight of material during a treatment time of 15 minutes to 2 hours.

14. A method according to claim 13, in which the starting material has an average diameter of 100–200 mm, a coefficient of variation of particle size of at least 48% and an angle of repose of 38–48°.

15. A method according to claim 11, in which water is added at a rate of from 25–30% by weight of material during a treatment time of 1 to 1.5 hours.

16. A method according to claim 15, in which the starting material has an average diameter of 100–200 mm, a coefficient of variation of particle size of at least 48% and an angle of repose of 38–48°.

* * * * *